United States Patent
Fujita et al.

(10) Patent No.: US 7,635,787 B2
(45) Date of Patent: Dec. 22, 2009

(54) PROCESS FOR PRODUCING METHIONINE

(75) Inventors: Kazuo Fujita, Ehime (JP); Kozo Onishi, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/054,789

(22) Filed: Mar. 25, 2008

(65) Prior Publication Data
US 2008/0242888 A1 Oct. 2, 2008

(30) Foreign Application Priority Data
Mar. 27, 2007 (JP) ............... 2007-081173

(51) Int. Cl.
*C07C 321/00* (2006.01)
(52) U.S. Cl. ..................................... 562/559
(58) Field of Classification Search ................. 562/559
See application file for complete search history.

(56) References Cited

U.S. PATENT DOCUMENTS 5,990,349 A * 11/1999 Geiger et al. ............... 562/559

FOREIGN PATENT DOCUMENTS

| EP | 0 780 370 A | 6/1997 |
| EP | 1 840 119 A2 | 10/2007 |
| EP | 1 849 769 A | 10/2007 |
| JP | 11-189582 * | 7/1999 |
| JP | 11-217370 A | 8/1999 |
| JP | 2003-104961 A | 4/2003 |
| JP | 2003-104962 * | 4/2003 |

* cited by examiner

*Primary Examiner*—Jafar Parsa
(74) *Attorney, Agent, or Firm*—Sughrue Mion, PLLC

(57) ABSTRACT

A process for producing methionine by hydrolysis of 5-(β-methylmercaptoethyl)hydantoin in the presence of an alkali, in which the concentration of hydrogen sulfide is 5 ppm or less in a solution used for hydrolysis comprising 5-(β-methylmercaptoethyl)hydantoin and the alkali, whereby methionine can be stably produced for a long period of time.

2 Claims, No Drawings

PROCESS FOR PRODUCING METHIONINE

FIELD OF THE INVENTION

The present invention relates to a process for producing methionine comprising hydrolyzing 5-(β-methylmercaptoethyl)hydantoin, in which the corrosion of an apparatus is prevented in steps relating to the hydrolysis.

BACKGROUND ART

A process for producing methionine by the hydrolysis of 5-(β-methylmercaptoethyl)hydantoin (hereinafter referred to as "M-hydantoin") is usually carried out according to the following reaction scheme in the presence of an alkali such as potassium carbonate:

Reaction Scheme

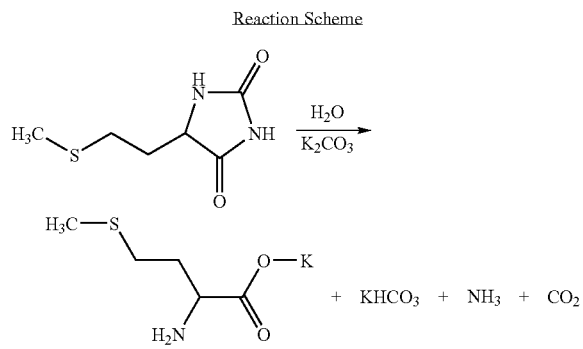

+ KHCO₃ + NH₃ + CO₂

In general, the reaction conditions for this hydrolysis reaction include a pressure of about 0.5 to 1.5 MPaG and a temperature of 150 to 200° C. The corrosion resistance of metallic materials under these hydrolysis conditions and also under conditions for operating associated apparatuses including, for example, preheating for hydrolysis and the treatment of exhaust gas is extremely strict regardless of whether the hydrolysis proceeds in a liquid phase or a gas phase. Therefore, for the construction of the apparatuses, from the viewpoint of having superior corrosion resistance to that of SUS304L stainless steel, austenite chromium-nickel stainless steel, titanium, zirconium, and duplex stainless steel comprising 21.0 to 30.0% by weight of chromium, 4.5 to 11.0% by weight of nickel, 2.5 to 5.0% by weight of molybdenum and 0.05 to 0.35% by weight of nitrogen as chemical components in the steel (cf. JP-A-11-217370) are used. Among them, the stainless steel described in JP-A-11-217370 is often utilized since it is less expensive than titanium and zirconium and has excellent corrosion resistance even at a high temperature. However, in or after the preheating step for hydrolysis, the temperature sometimes rises to 120° C. or higher. In such a case, a solution subjected to the hydrolysis may induce the corrosion of materials, which may result in the corrosion of the metallic materials of the apparatuses and the coloring of products due to metal ions eluted from the metallic materials by corrosion.

SUMMARY OF THE INVENTION

An object of the present invention is to provide a process for producing methionine stably for a long period of time by preventing the corrosion of apparatuses used for the production of methionine by the hydrolysis of M-hydantoin at a high temperature.

The present invention provides a process for producing methionine comprising the step of hydrolyzing 5-(β-methylmercaptoethyl)hydantoin in the presence of an alkali, wherein a concentration of hydrogen sulfide is 5 ppm or less in a solution used for hydrolysis comprising 5-(β-methylmercaptoethyl)hydantoin and the alkali.

In one preferred embodiment of the present invention, the concentration of hydrogen sulfide in a solution used for hydrolysis comprising 5-(β-methylmercaptoethyl)hydantoin and the alkali is measured and adjusted to 5 ppm or less, and then the solution is used for hydrolysis.

The method of the present invention can stably produce methionine for a long period of time by the hydrolysis of M-hydantoin in the presence of an alkali.

DETAILED DESCRIPTION OF THE INVENTION

In general, M-hydantoin is prepared by reacting methyl mercaptane with acrolein to give 3-methylmercaptopropionaldehyde (hereinafter abbreviated as "MAD"), then subjecting MAD to cyanhydrination with hydrogen cyanide to give 3-methylmercaptopropioncyanhydrin (hereinafter referred to as "MCH"), and subjecting MCH to hydantoination using carbon dioxide and ammonia. The sources of carbon dioxide and ammonia used in the step for hydantoination may be those conventionally used. For example, carbon dioxide and ammonia, ammonium carbonate or ammonium bicarbonate are used in excessive amounts to MCH, preferably 1 to 4 times amounts of the stoichiometric amounts. In the preparation of M-hydantoin, general conditions include a reaction temperature of from about 60 to about 85° C. and a residence time of from about 3 to about 6 hours, etc.

M-Hydantoin is then hydrolyzed in the presence of an alkali such as an alkali metal hydroxide (e.g., sodium hydroxide, potassium hydroxide, etc.), an alkali metal carbonate (e.g., sodium carbonate, potassium carbonate, etc.), an alkali metal hydrogencarbonate (e.g., sodium hydrogencarbonate, potassium hydrogencarbonate, etc.) to form an alkali metal salt of methionine. The hydrolysis is usually carried out under a pressure of from about 0.5 to about 1.5 MPaG at a temperature of from about 150 to about 200° C. for from about 10 to about 120 minutes. Ammonia and carbon dioxide liberated during hydrolysis may be recovered and recycled to the process for preparing M-hydantoin.

Then, the obtained hydrolysis liquid is neutralized by adding an acid or an acidic substance such as sulfuric acid, hydrochloric acid, or carbon dioxide to the liquid so as to crystallize methionine. The precipitated methionine is filtered and separated, optionally washed with water and dried to obtain methionine as a final product.

During the operation of the present invention, the steps relating to hydrolysis are carried out at a hydrogen sulfide concentration of 5 ppm or less in the solution comprising M-hydantoin and the alkali to be subjected to the hydrolysis.

A method for removing hydrogen sulfide from the solution is not specifically limited, and hydrogen sulfide may be removed by a conventional method such as distillation and rectification. Alternatively, the following method may be used to remove hydrogen sulfide.

In such a process for producing methionine, it is presumed that hydrogen sulfide may usually be derived from the step for producing MAD. MAD is obtained by the reaction of methyl mercaptane and acrolein, and MAD containing hydrogen sulfide at a low concentration or substantially no hydrogen sulfide can be obtained by using the excessive amount of acrolein relative to methyl mercaptane. Therefore, in the present invention, the solution of M-hydantoin containing hydrogen sulfide at a low concentration, which will be subjected to the hydrolysis, can be generally prepared using MAD containing hydrogen sulfide at a low concentration, or can be preferably prepared by using MAD containing substantially no hydrogen sulfide obtained by increasing the amount of acrolein relative to methyl mercaptane in the process for the preparation of MAD, although the total production cost increases. Alternatively, when the concentration of hydrogen sulfide in MAD is high, it is possible to add a substance which can remove hydrogen sulfide (e.g., acrolein, etc.) to MAD to decrease the concentration of hydrogen sulfide. Of course, when hydrogen sulfide is present in the alkali which is used together with M-hydantoin, hydrogen sulfide may be removed from the alkali, or an alternative alkali containing substantially no hydrogen sulfide may be used, so that the concentration of hydrogen sulfide in the solution to be subjected to hydrolysis is adjusted to 5 ppm or less.

The process of the present invention preferably comprises a step for measuring the concentration of hydrogen sulfide in the solution used for hydrolysis containing M-hydantoin and the alkali and adjusting the concentration of hydrogen sulfide in the solution to 5 ppm or less. The concentration of hydrogen sulfide in the solution used for hydrolysis containing M-hydantoin and the alkali may be calculated by separately measuring the concentrations of hydrogen sulfide in M-hydantoin and the alkali, and summing them up. Furthermore, as a method for adjusting the concentration of hydrogen sulfide in the solution to 5 ppm or less, as described above, the concentrations of hydrogen sulfide in M-hydantoin and the alkali are separately adjusted to 5 ppm or less and then M-hydantoin and the alkali are mixed.

In the present invention, the steps relating to the hydrolysis, in which the countermeasure against hydrogen sulfide is employed, refer to steps following the step for hydantoination and up to the step for hydrolysis, and include a step for preheating for hydrolysis provided between the step for hydantoination and the step for hydrolysis. As a material of the apparatuses to be used in these steps, duplex stainless steel is preferably used, more preferably, duplex stainless steel comprising 21.0 to 30.0% by weight of chromium, 4.5 to 11.0% by weight of nickel, 2.5 to 5.0% by weight of molybdenum and 0.05 to 0.35% by weight of nitrogen as chemical components in the steel is used, more preferably, SUS329J4L, SCS10, UNS S39274, UNS S31260, UNS S32550, UNS S32760, UNS S32900, UNS S32950, UNS S39277 or UNS S32750 is used. Among them, SUS329J4L is particularly preferably used.

EXAMPLES

Hereinafter, the process of the present invention is explained in more detail by the following examples, which will not limit the scope of the present invention in any way.

Example 1

5-(β-Methylmercaptoethyl)hydantoin was prepared by the hydantoination of 3-methylmercaptopropioncyanhydrin with ammonium carbonate made from carbon dioxide and ammonia, and potassium carbonate was mixed with 5-(β-Methylmercaptoethyl)hydantoin to obtain a solution (M-hydantoin concentration: about 9 wt. %; potassium carbonate concentration: about 10% by weight; hydrogen sulfide concentration: less than the detection limit). This solution was used as a standard test solution. To the standard test solution, an aqueous hydrogen sulfide solution having a known concentration was added to give a test solution shown in Table 1.

A test specimen made of SUS329J4L (DP-3® manufactured by Sumitomo Metal Industries, Ltd.) was immersed in the liquid-phase portion of a one-liter autoclave. A corrosion test was carried out by charging 600 ml of each test liquid and maintaining it for 20 hours at 120° C.

The weight of the test specimen was measured before and after the corrosion test, and the corrosion rate was calculated according to the following equation:

$$\text{Corrosion rate (mm/year)} = \{[(W_1 - W_2)/(d \times S)]/\text{test time (hrs)}\} \times 8760$$

$W_1$: Weight (g) of a test specimen before corrosion test
$W_2$: Weight (g) of a test specimen after corrosion test
d: Density (g/mm$^3$) of a test specimen
S: Surface area (mm$^2$) of a test specimen In addition, a corroded state of the test specimen was visually observed. The results are shown in Table 1.

TABLE 1

| Test solution | Corrosion rate (mm/year) | Degree of corrosion |
|---|---|---|
| Standard test liquid | 0.01 | Small, Passive state No problem |
| Standard test liquid + 8 ppm hydrogen sulfide | 0.99 | Large, Active state General corrosion |
| Standard test liquid + 6 ppm hydrogen sulfide | 1.01 | Large, Active state General corrosion |
| Standard test liquid + 5 ppm hydrogen sulfide | 0.01 | Small, Passive state No problem |
| Standard test liquid + 3 ppm hydrogen sulfide | 0.00 | Small, Passive state No problem |

As is apparent from Table 1, the test solutions comprising M-hydantoin and the alkali having a hydrogen sulfide concentration exceeding 5 ppm corroded the test specimen, while the test specimens were not corroded when the hydrogen sulfide concentration in the test solution was 5 ppm or less.

The invention claimed is:

1. A process for producing methionine comprising the step of:
   reacting methyl mercaptane with acrolein to obtain 3-methylmercaptopropionaldehyde,
   subjecting 3-methylmercaptopropionaldehyde to cyanhydrination with hydrogen cyanide to obtain 3-methylmercaptopropioncyanhydrin,
   subjecting 3-methylmercaptopropioncyanhydrin to hydantoination using carbon dioxide and ammonia to obtain 5-(β-methvlmercaptoethyl)-hydantoin, and
   hydrolyzing 5-(β-methylmercaptoethyl)hydantoin in the presence of an alkali,
   wherein a concentration of hydrogen sulfide is lowered to 5 ppm or less in a solution used for hydrolysis comprising 5-(β-methylmercaptoethyl)hydantoin and the alkali by at least one of the following methods:
   1) distillation or rectification of the solution comprising 5-(β-methylmercaptoethyl)hydantoin and the alkali;
   2) use of an excessive amount of acrolein relative to methyl mercaptane during the reaction of methyl mercaptane with acrolein;
   3) addition of a substance for removing hydrogen sulfide.

2. The process according to claim 1, which further comprises a step of measuring the concentration of hydrogen sulfide in the solution used for hydrolysis comprising 5-(β-.methylmercaptoethyl)hydantoin and the alkali and adjusting the concentration of hydrogen sulfide in the solution to 5 ppm or less, prior to the use of the solution for hydrolysis.

* * * * *